(12) United States Patent
Goto et al.

(10) Patent No.: US 6,515,141 B1
(45) Date of Patent: Feb. 4, 2003

(54) PROCESS FOR THE PREPARATION OF INDOLE DERIVATIVES OR SALTS THEREOF

(75) Inventors: Shunsuke Goto, Osaka (JP); Kazuo Ike, Osaka (JP); Kiyoaki Takasuka, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 303 days.

(21) Appl. No.: 10/049,651

(22) PCT Filed: Aug. 14, 2000

(86) PCT No.: PCT/JP00/05454

§ 371 (c)(1), (2), (4) Date: Aug. 26, 1999

(87) PCT Pub. No.: WO01/16101

PCT Pub. Date: Mar. 8, 2001

(30) Foreign Application Priority Data

Aug. 26, 1999 (JP) .......................................... 11/239428

(51) Int. Cl.⁷ ............................................. C07D 403/06
(52) U.S. Cl. ...................................................... 548/492
(58) Field of Search ........................................... 548/492

(56) References Cited

U.S. PATENT DOCUMENTS 5,013,837 A   5/1991   Ward et al.

FOREIGN PATENT DOCUMENTS

| EP | 149419 | 7/1985 |
| EP | 171037 | 2/1986 |
| EP | 0592438 B1 * | 8/1997 |
| WO | 96/07660 | 3/1996 |

OTHER PUBLICATIONS

E. Wenkert et al.: "Yuehchukene analogues" J. Org. Chem., vol. 53, pp. 3170–3177 1988.

* cited by examiner

*Primary Examiner*—Joseph K. McKane
*Assistant Examiner*—Andrea D. Small
(74) *Attorney, Agent, or Firm*—Oblon, Spivak, McClelland, Maier & Neustadt, P.C.

(57) ABSTRACT

This invention provides a novel process for the preparation of a 3-acylindole or the salt thereof in a high yield.

3 Claims, No Drawings

PROCESS FOR THE PREPARATION OF INDOLE DERIVATIVES OR SALTS THEREOF

This application is a 371 of PCT/JP00/05454 Aug. 14, 2000.

TECHNICAL FIELD

This invention relates to a novel process for the preparation of a 3-acylindole or the salt thereof useful for various synthetic intermediates or bioactive compounds.

BACKGROUND ART

Acylation into the 3 position of an indole is conducted by conventional and general processes, such as Friedel-Crafts and Vilsmeier reactions. However, the indole is unstable in an acidic condition, for example in the presence of a Lewis acid, and decomposition occurs at the same time. Hence, the yield of the product is very low. Furthermore, in the case of a reaction conducted via an indolemagnesium intermediate using a Grignard reagent, the product generally cannot be obtained in a high yield. In an example of benzoyl chloride, the yield is low, 32%, according to C. Alberti, Gazz. Chim. Ital. 89, 1033 (1959). According to a recent report for solving this problem by C. Yang et al., Synthetic Communications, 27, 2125 (1997), an indolemagnesium intermediate is further converted into an indolezinc intermediate, and the intermediate undergoes a reaction in the presence of a Lewis acid, whereby the product is obtained in a high yield of 77%. However, the operations for this process are complicated. In addition, methylene chloride, Lewis acid and zinc, which may cause problems in environmental protection, are required to be processed. Hence, this process has many problems as an industrial synthesis process. In order to develop an industrial synthesis process that can be carried out at low cost without causing environmental problems, the inventors of this invention have made studies mainly on improvement in yield in an acylation reaction via an indolemagnesium intermediate.

SUMMARY OF THE INVENTION

This invention is intended to provide a novel process for the preparation of a 3-acylindole or the salt thereof at a high yield.

The inventors of this invention have made various studies on the reaction conditions of a Grignard reaction via an indolemagnesium intermediate.

Regarding an addition process, an acylation agent is added to an indolemagnesium intermediate according to literature. However, it was found that a high yield was obtained by reversing the order of the addition, that is, by adding the indolemagnesium intermediate to the acylation agent. Furthermore, the inventors of this invention have also made studies on reaction solvents, the preparation of a Grignard reagent, reaction temperatures, etc.

DISCLOSURE OF THE INVENTION

This invention relates to a process for the preparation of a 3-acylindole or the salt thereof by obtaining an intermediate activated by adding a Grignard reagent prepared by the action of an alkyl halide and magnesium in the presence of a base in a hydrocarbon-based solvent to an indole or the salt thereof under cooling, and by reacting the intermediate with an acylation agent under cooling.

As a result of studies on the industrial synthesis process for the 3-acylindole, the inventors of this invention have found that the 3-acylindole or the salt thereof can be obtained economically, excellently in environmental protection and easily in operation by obtaining an intermediate activated by adding the Grignard reagent prepared by the action of an alkyl halide and magnesium in the presence of a base in a hydrocarbon-based solvent to an indole or the salt thereof under cooling, and by reacting the intermediate with an acylation agent under cooling, and have completed this invention suited for synthesis in large volume.

Suitable salts for the compounds used for this invention are conventional non-toxic salts and include an acid addition salt such as an organic acid salt (e.g. acetate, trifluoroacetate, maleate, tartrate, methanesulfonate, benzenesulfonate, formate, toluenesulfonate, etc.) and an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), and the like.

Th e process for the preparation in accordance with this invention will be described below in detail.

The 3-acylindole or the salt thereof can be produced by obtaining an intermediate activated by adding the Grignard reagent prepared by the action of an alkyl halide and magnesium in the presence of a base in a hydrocarbon-based solvent to an indole or the salt thereof under cooling, and by reacting the intermediate with an acylation agent under cooling.

The acylation agent used for this invention is an acid halide that is used in the form of an acid chloride in particular. Suitable "acyl group" of the acylation agent may include a conventional acyl group used in the chemical field, for example, aromatic acyl such as benzil that may be substituted.

The hydrocarbon-based solvent may include, for example, benzene, toluene, hexane, heptane, etc.

Alkyl halide may include, for example, ethyl iodide, n-butyl iodide, n-propyl bromide, i-propyl bromide, etc.

The reaction is carried out in the presence of an inorganic base or an organic base, for example, alkali metal hydrogencarbonate, tri(lower)alkylamine, pyridine, N-(lower)alkylmorpholine, N,N-di(lower)alkylbenzilamine, etc., in which triethylamine is preferable.

The reaction temperature is not critical and the reaction is usually carried out under cooling, preferably below 20° C., more preferably below 10° C.

The compound obtained according to the above-mentioned process can be isolated and purified in a conventional manner, for example, pulverization, recrystalization, column chromatography, reprecipitation, and the like.

This invention will be described in more detail in accordance with the following examples.

EXAMPLE 1

Magnesium (2.08 g), toluene (40 ml), triethylamine (10.4 g) were put into a 3" diameter flask, and the internal temperature was raised to 30 to 45° C. A solution of 1-iodebutane (18.9 g) in toluene was added under stirring at an internal temperature of 30 to 45° C. After stirring for two hours at the same temperature, the temperature was lowered to 0 to 5° C., thereby preparing a solution of iode n-butylmagnesium in toluene. To this prepared Grignard reagent, indole (10.0 g) dissolved beforehand in toluene (25 ml) was added at an internal temperature of 0 to 10° C., and a reaction was carried out for about one hour at the same temperature to synthesize iodeindole-1-ylmagnesium. Then, m-nitrobenzoyl chloride (15.8 g) and toluene (60 ml) were put into another 3" diameter flask, and the internal temperature was lowered to below −15° C. The slurry of the iodeindole-1-ylmagnesium prepared previously was added to the solution of this acid chloride while keeping the internal temperature at −15 to −10° C., and the mixture was stirred for more one hour at the same temperature. The internal temperature was then raised further to 20 to 25° C., and the mixture was stirred for one hour. After this reaction, the mixture was added to an aqueous ammonium chloride solution (16 g, 60 ml) prepared beforehand in another 3" diameter flask at 10° C. or less to carry out quenching. Acetone (220 ml) was added thereto, the internal temperature was raised to 50 to 65° C., and dissolution was carried out, followed by separation. The organic layer of the upper layer was then collected and cleaned with an aqueous 5% sodium hydrogencarbonate solution at the same temperature. The solvent was evaporated so as to be concentrated to about 50 ml. After cooled to an internal temperature of 2 to 10° C., a precipitated crystal was filtered. The filtered crystal was cleaned with toluene (10 ml) and dried to obtain a crystal of 3-m-nitrobenzoylindole (18.2 g) (80.0% yield).

NMR (DMSO-$d_6$, δ): 7.2–7.3 (2H, m), 7.5–7.6 (1H, m), 7.84 (1H, t, J=7.9 Hz), 8.10 (1H, s), 8.2–8.3 (2H, m), 8.3–8.5 (2H, m), 12.24 (1H, br, s); MASS (M+1): 267.

EXAMPLE 2

Magnesium (2.08 g), toluene (40 ml), triethylamine (10.4 g) were put into a 3" diameter flask, and the internal temperature was raised to 30 to 45° C. A solution of 1-iodebutane (18.9 g) in toluene was added under stirring at an internal temperature of 30 to 45°C. After stirring for two hours at the same temperature, the temperature was lowered to 0 to 5° C., thereby preparing a solution of iode n-butylmagnesium in toluene. To this prepared Grignard reagent, indole (10.0 g) dissolved beforehand in toluene (25 ml) was added at an internal temperature of 0 to 10° C., and a reaction was carried out for about one hour at the same temperature to synthesize iodeindole-1-ylmagnesium. Then, benzoyl chloride (12.0 g) and toluene (60 ml) were put into another 3" diameter flask, and the internal temperature was lowered to below −15° C. The slurry of the iodeindole-1-ylmagnesium prepared previously was added to the solution of this acid chloride while keeping the internal temperature at −15 to −10° C., and the mixture was stirred for more one hour at the same temperature. The internal temperature was then raised further to 20 to 25° C., and the mixture was stirred for one hour. After this reaction, the mixture was added to an aqueous ammonium chloride solution (16 g, 60 ml) prepared beforehand in another 3" diameter flask at 10° C. or less to carry out quenching. Acetone (220 ml) was added thereto, the internal temperature was raised to 50 to 65° C., and dissolution was carried out, followed by separation. The organic layer of the upper layer was then collected and cleaned with an aqueous 5% sodium hydrogencarbonate solution at the same temperature. The solvent was evaporated so as to be concentrated. Methanol (20 ml) was added thereto and refluxed. After cooled to an internal temperature of 2 to 10° C., a precipitated crystal was filtered. The filtered crystal was cleaned with cooled methanol (5 ml) and dried to obtain a crystal of 3-benzoylindole (13.7 g) (72.2% yield).

NMR (DMSO-$d_6$, δ): 7.2–7.6 (6H, m), 7.70 (1H, d, J=3.0 Hz), 7.8 (2H, m), 8.4 (1H, m); MASS (M+1): 222.

The preparation process in accordance with this invention is made up as described above, and can prepare a 3-acylindole or the salt thereof useful for various synthetic intermediates or bioactive compounds in a yield far higher than those of conventional processes. In addition, it is not necessary to use ether as a solvent, thereby offering an effect of not causing environmental problems.

What is claimed is:

1. A process for the preparation of a 3-acylindole or the salt thereof by obtaining an intermediate activated by adding a Grignard reagent prepared by the action of an alkyl halide and magnesium in the presence of a base in a hydrocarbon-based solvent to an indole or the salt thereof under cooling, and by reacting said intermediate with an acylation agent under cooling.

2. A process in accordance with claim 1, wherein a hydrocarbon-based solvent is toluene, a base is triethylamine, an alkyl halide is alkyl iodide, and an acylation agent is acid halide.

3. A process in accordance with claim 2, wherein an acid halide is acid chloride.

* * * * *

UNITED STATES PATENT AND TRADEMARK OFFICE
CERTIFICATE OF CORRECTION

PATENT NO. : 6,515,141 B1
DATED : February 4, 2003
INVENTOR(S) : Goto et al.

It is certified that error appears in the above-identified patent and that said Letters Patent is hereby corrected as shown below:

<u>Title page,</u>
Item [*] Notice:, "Subject to any disclaimer, the term of this patent is extended or adjusted under 35 USC 154(b) by (303) days", delete the phrase "by 303 days" and insert -- by 0 days --

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,515,141 B1
DATED : February 4, 2003
INVENTOR(S) : Goto et al.

It is certified that error appears in the above-identified patent and that said Letters Patent is hereby corrected as shown below:

<u>Title page,</u>
Item [86], the Filing Date should read:
-- [86]  PCT No.:  PCT/JP00/05454

§ 371 (c)(1),
   (2), (4) Date:  May 24, 2002 --

Signed and Sealed this

Eleventh Day of November, 2003

JAMES E. ROGAN
*Director of the United States Patent and Trademark Office*